(12) United States Patent
Olgiati et al.

(10) Patent No.: US 9,743,941 B2
(45) Date of Patent: Aug. 29, 2017

(54) DEVICE FOR PATELLAR RESURFACING

(75) Inventors: Gianluca Olgiati, Como (IT);
Massimiliano Bernardoni, Figino (CH); Francesco Siccardi, Sonvico (CH); Alberto Siccardi, Sonvico (CH)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 695 days.

(21) Appl. No.: 14/364,766

(22) PCT Filed: Jun. 21, 2012

(86) PCT No.: PCT/IB2012/001239
§ 371 (c)(1),
(2), (4) Date: Jul. 10, 2014

(87) PCT Pub. No.: WO2012/176054
PCT Pub. Date: Dec. 27, 2012

(65) Prior Publication Data
US 2014/0358148 A1 Dec. 4, 2014

(30) Foreign Application Priority Data
Jun. 22, 2011 (CH) ...................................... 1062/11

(51) Int. Cl.
*A61F 5/00* (2006.01)
*A61B 17/17* (2006.01)
*A61B 17/15* (2006.01)

(52) U.S. Cl.
CPC ........ *A61B 17/1767* (2013.01); *A61B 17/158* (2013.01)

(58) Field of Classification Search
None
See application file for complete search history.

(56) References Cited

U.S. PATENT DOCUMENTS 4,502,483 A 3/1985 Lacey
5,021,055 A 6/1991 Burkinshaw et al.
(Continued)

FOREIGN PATENT DOCUMENTS

EP 1833387 9/2007
EP 2198789 6/2010
(Continued)

OTHER PUBLICATIONS

Laskin, "Alignment of Total Knee Components," Orthopedics, vol. 7, Issue 1, Jan. 1984, Abstract only, 3 pages.
(Continued)

*Primary Examiner* — Sameh Boles
(74) *Attorney, Agent, or Firm* — Allen, Dyer, Doppelt & Gilchrist, P.A.

(57) ABSTRACT

The device, tool, instrument and the like, for patellar resurfacing, according to the invention, comprises at least one bearing framework (IN), which incorporates a cutting slot (Tpg) and a lower support guide (G2) which may assume different positions with respect to the center of the patellar articular surface. The device is completed by an upper support guide (G1) of the patella for maintaining the shape-constraint coupling between the bearing framework and the patella. Advantageously the device uses the peripheral surface (and not the central one) of said patella, guaranteeing minimal invasiveness and perfect visibility.

10 Claims, 4 Drawing Sheets

(56) References Cited

U.S. PATENT DOCUMENTS

| | | | |
|---|---|---|---|
| 5,624,444 A | 4/1997 | Wixon et al. | |
| 5,716,361 A | 2/1998 | Masini | |
| 6,033,410 A | 3/2000 | McLean et al. | |
| 6,468,280 B1 | 10/2002 | Saenger et al. | |
| 6,916,325 B2 | 7/2005 | Kana et al. | |
| 6,928,742 B2 | 8/2005 | Broers et al. | |
| 7,534,263 B2 * | 5/2009 | Burdulis, Jr. | A61B 17/155 606/88 |
| 8,355,773 B2 | 1/2013 | Leitner et al. | |
| 8,425,524 B2 | 4/2013 | Aker et al. | |
| 2002/0029038 A1 | 3/2002 | Haines | |
| 2003/0212403 A1 | 11/2003 | Swanson | |
| 2005/0228393 A1 | 10/2005 | Williams, III et al. | |
| 2006/0142774 A1 | 6/2006 | Metzger | |
| 2006/0184177 A1 | 8/2006 | Echeverri | |
| 2007/0288030 A1 | 12/2007 | Metzger et al. | |
| 2008/0097450 A1 | 4/2008 | Brown et al. | |
| 2008/0234664 A1 | 9/2008 | May et al. | |
| 2009/0143783 A1 | 6/2009 | Dower | |
| 2010/0030223 A1 * | 2/2010 | Keller | A61B 17/1767 606/99 |
| 2010/0145344 A1 | 6/2010 | Jordan et al. | |
| 2010/0191244 A1 | 7/2010 | White et al. | |
| 2011/0160736 A1 | 6/2011 | Meridew et al. | |
| 2012/0130382 A1 | 5/2012 | Iannotti et al. | |
| 2012/0277751 A1 | 11/2012 | Catanzarite et al. | |
| 2012/0310246 A1 | 12/2012 | Belcher et al. | |
| 2014/0081275 A1 | 3/2014 | Metzger et al. | |

FOREIGN PATENT DOCUMENTS

| | | |
|---|---|---|
| WO | 2006060795 | 6/2006 |
| WO | 2007/097854 | 8/2007 |
| WO | 2009045960 | 4/2009 |

OTHER PUBLICATIONS

Dennis et al, "Gap Balancing Versus Measured Resection Technique for Total Knee Arthroplasty," Clin. Orthop. Relat. Res, 2010, 468, pp. 102-107.

* cited by examiner

DEVICE FOR PATELLAR RESURFACING

FIELD OF APPLICATION

The present invention refers to devices, equipment, instruments and the like for patellar resurfacing under mini-invasiveness conditions so as not to cause discomfort in specific patients, and a good visual control by the operator so as to allow —at any stage and time— the assessment of the surgery plan in an extremely accurate manner.

More in detail, the finding regards systems for patellar resurfacing with specific geometries for the univocal coupling with the anatomic structure of the single patients, said systems consisting in at least one device with a first portion which is coupled in a univocal manner to the articular face of the patella, at least one second part or main support portion provided so that said shape-constraint coupling with the aforementioned first part is maintained, and patella forceps (conventional or unconventional).

STATE OF THE ART

Equipment, devices, systems, instruments and the like of the aforementioned type are mutually described in literature and widely used daily.

These known systems doubtlessly have improved surgery techniques, but these historical advantages are still associated to a considerable number of drawbacks including those regarding the fact that they are still too invasive and thus causing discomfort to the patient to name but a few. Actually, this lead to a close relation between the invasiveness of the equipment (conventional, especially if not up to the state of the art) and the frequency and seriousness of the discomfort on the patients. Another considerable drawback lies in the ensuing poor visibility of the bone of the patient during the positioning of the patellar guide which often jeopardizes the critical aspect of obtaining good results in terms of accuracy and repeatability.

PRIOR ART

As mentioned previously, the literature regarding knee arthroprosthesis and in particular patellar resurfacing is quite extensive and complex, a major part of it is still under assessment especially in the USA, UE and CN and solely the most significant and available cases among those mentioned hereinafter shall be mentioned regardless of the chronological order of occurrence thereof.

The International patent application PCT/US2007/001624 filed on Jan. 1, 2007 and Published as WO2007/097854 describes arthroplasty devices comprising a guide body (Jig) configured to be aligned to the surface of a bone, and a positioning component configured to provide a visible, audible or tactile indication when said guide body is aligned with the bone surface. In different embodiments said Jig may comprise a rod, and the guide body may comprise an opening while the positioning component comprises a projection which extends through the guide body.

The International Patent Application PCT/US2008/0781443 filed on Sep. 29, 2008 and Published as WO2009/045960 regards a femoral cutting block which allows the operator to check whether the positioning of said block was carried out correctly. For such purpose the block is provided with a first guide (conventional) and with a second guide which extends —at the rear part— from the front body and which defines a window between the guides which have a first and a second tab which is engaged with the distal front and rear surfaces. The femur is used as the support base for the alignment of the knee ligaments.

In U.S. Pat. No. 7,534,263 (filed on Dec. 2, 2004 corresponding to WO2006/060795 and EP 1833387) claims a guide for engaging the surface of a patella, said guide comprising a mould having a first surface configured to be adapted to the surface of said patella, which is thus specific for each patient, has an ad hoc opening substantially at the centre of said guide (but, regardless this, it may have an insignificant eccentricity). The aforementioned mould has a plurality of openings. In said patent EP1833387 (page 40) the fact is highlighted that the relative description contains 18 patent references and 12 non-patent literature references. Thus, it is difficult to mention, not even briefly, the 30 paragraphs of possible interest among these 30 prior art documents.

SUMMARY OF THE INVENTION

The first object of the present invention is to provide a device for patellar resurfacing, not having the previously mentioned drawbacks, in particular having invasiveness such as not to cause discomfort to the patient.

Still another object is that of allowing, at any stage and time, the assessment of the surgery plan in an extremely accurate manner and without the possibility of evident errors due to the optimal visibility guaranteed by the system.

The device according to the invention is characterised by:
a base for supporting the ligaments defined by the patella;
a bearing framework IN which incorporates a cutting slot Tpg;
a guide G2 for the lower support of said ligaments; and
an upper support guide G1, which is generally made in a single piece with said framework IN.

BRIEF DESCRIPTION OF THE DRAWINGS

The various aspects and advantages of the invention will be more apparent from the description of the represented embodiments (given by way of non-limiting example) in the reference drawings wherein:

FIG. 1 is the schematic representation of the ligaments (isolated from any support) in perspective top view; FIG. 2 is a top perspective view of a support of the lower part of said ligaments; FIG. 3 is a top perspective view of the major component of the device according to the invention which is a resection guide G1 in which there is an upper coupling guide.

FIG. 5 is the view of the compacted device of the framework of FIG. 3 and of the lower support guide associated thereto.

DETAILED DESCRIPTION OF THE INVENTION

By way of outlining the ideas clearly, the patellar resurfacing device according to the invention, comprises as components: —a lower support guide G2; —an upper support guide G1; and —a framework IN.

Figure 1:
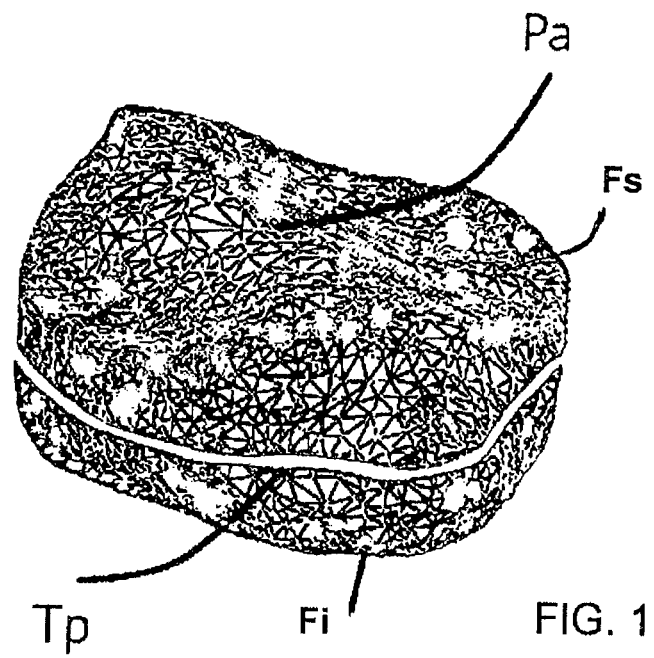
FIGS. 1, 2, 3 and 5 are schematic views of tools according to the invention. More in particular.

Solely by way of example, said patellar resurfacing device may comprise a patella Pa with patellar cutting Tp, schematically represented in the top perspective view of FIG. 1, in which Fs and Fi indicate the upper and lower surfaces thereof.

Figure 2:
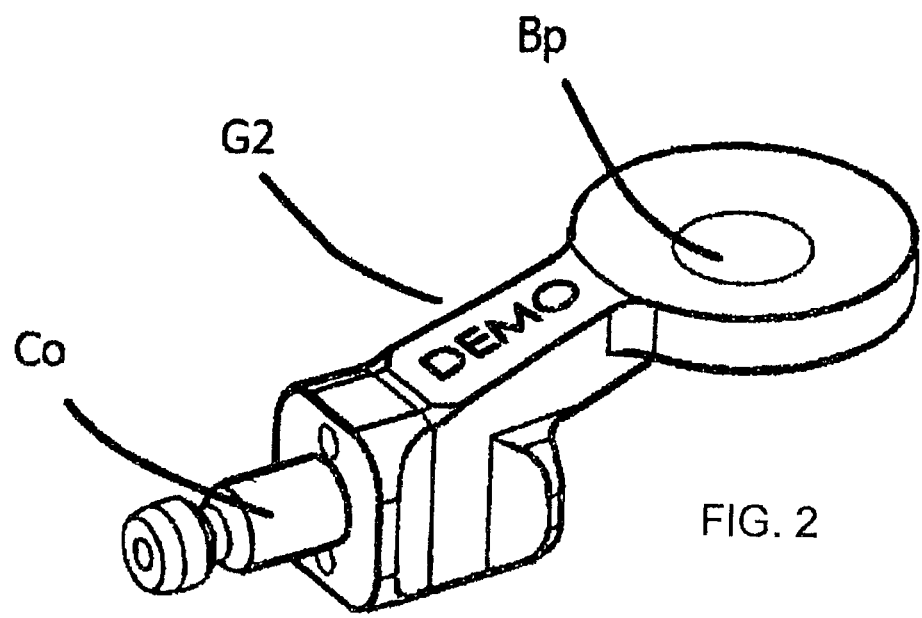

FIG. 2 represents the lower support guide G2 which comprises the central arm DEMO (FIG. 2) having —at one end— the lower concave support Bp and —on the other end— the connection Co with forceps.

Figure 3:
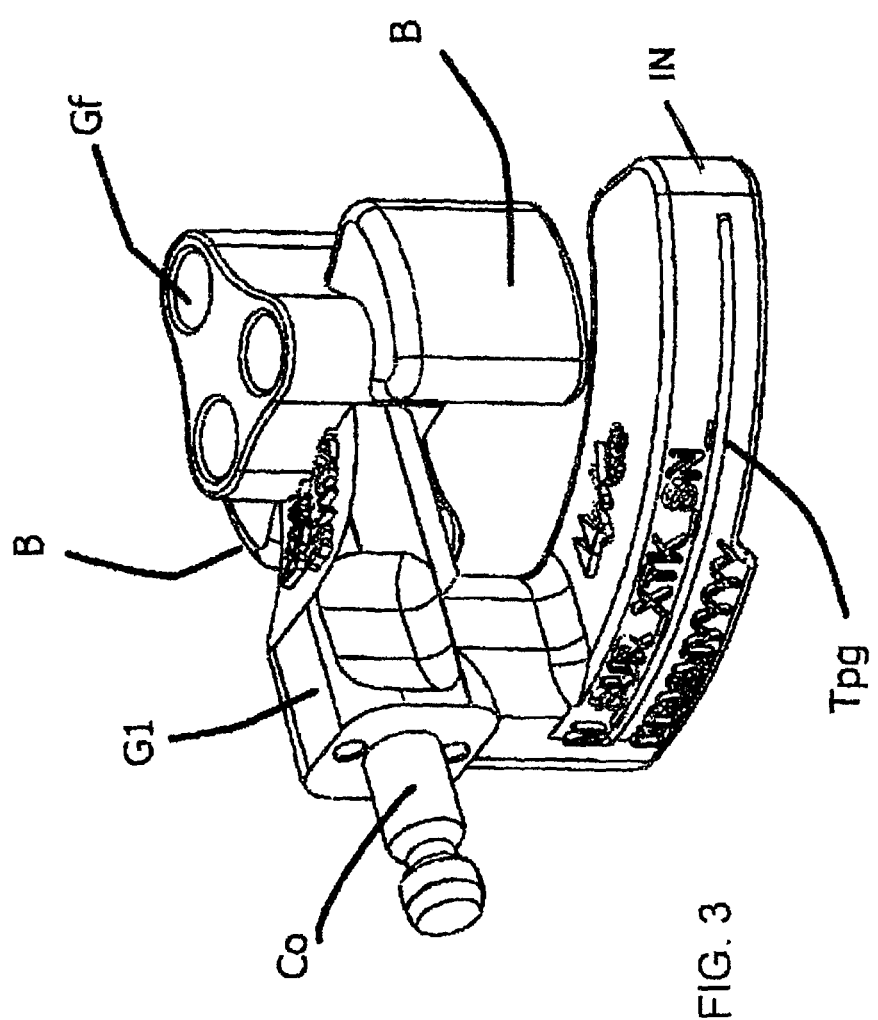

FIG. 3 represents the upper support guide G1 which comprises the resection device, the arms B,B for connecting to the bone through simple shape-coupling, the perforation/marking guide Gf for implant positioning reference, and the bone resection cutting slot Tpg. Also the upper support guide G1 comprises —at one end thereof— a connection for the coupling with patella forceps.

Figure 4:
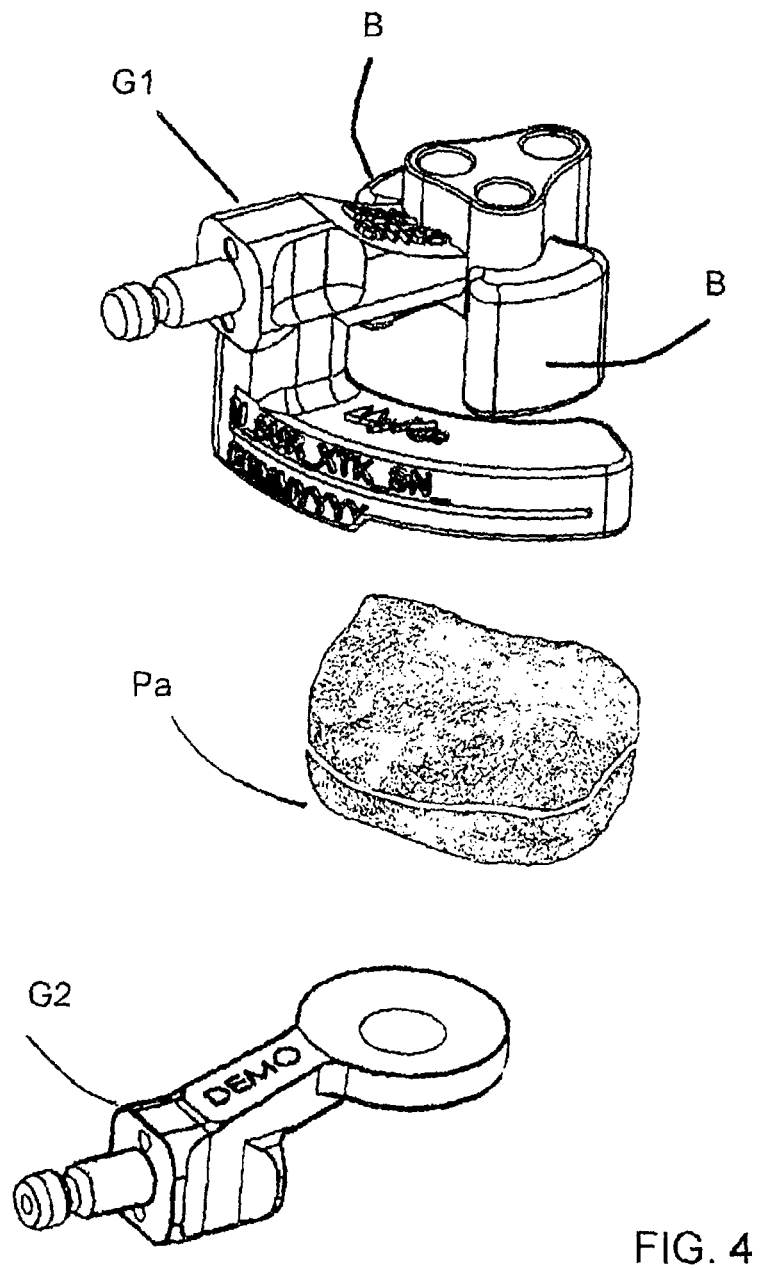
FIG. 4 is an exploded perspective view of the three components of FIGS. 1, 2 and 3, and lastly
Figure 5:
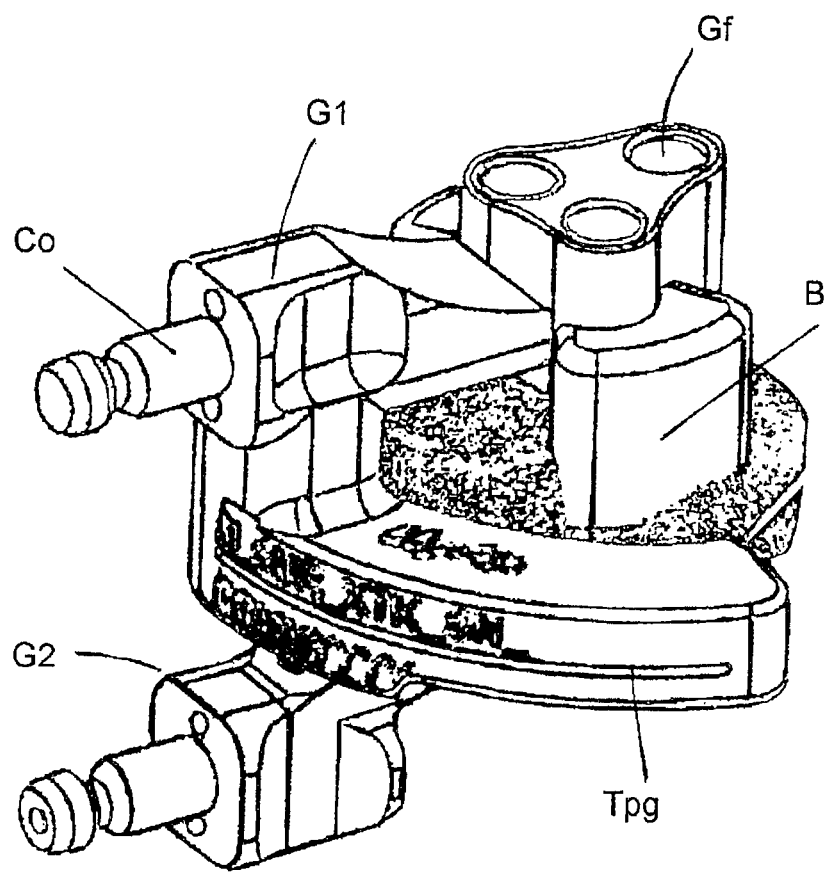

In FIG. 4 the aforementioned components (G1—upper support guide; the bone connection arms B,B, the patellar ligaments Pa and the lower support guide G2) are represented detached by explosion. The same components are represented combined and compacted by close assembly, as indicated in FIG. 5.

Characteristically, the patellar resurfacing according to the invention is articulated in a first coupling —in a univocal manner— of a part of the device to the articular face of the patella, and in a second portion thereof, mainly a support portion, provided so that the first shape-constraint coupling with the guide is maintained.

Contingently conventional patella forceps (not represented) may also be used which allows relatively constraining the upper support guide G1 and the lower support guide G2. Typically, the resection guide is provided with a plurality of holes, besides a "slot", for directly receiving at least one cutting blade.

Advantageously the perforation guide part is not fixed, but it may assume different positions with respect to the centre of the articular face.

The invention has been described with particular reference to the embodiments represented in the drawings; however, it may be subjected to all replacements, additions and the like which for being within reach to a man averagely skilled in the art shall be deemed included and/or falling within the independent claims.

The invention claimed is:

1. A device for resurfacing a patella, the device comprising: a bearing framework defining a cutting slot; a lower support guide comprising first and second ends, said second end comprising a concave circular disc configured to support the patella, said first end comprises a lower forceps connection configured to receive a forceps; and an upper support guide extending parallel to a plane of said concave circular disc and configured to support the patella; said upper support guide being an integral monolithic unit with said bearing framework; said lower support guide comprising a straight medial portion between said first and second ends and being canted with respect to the plane of said concave circular disc.

2. The device according to claim 1, wherein said upper support guide has a plurality of openings therein.

3. The device according to claim 1, wherein the lower support guide is configured to assume a plurality of different positions with respect to a center of a patellar articular surface of the patella.

4. The device according to claim 1, wherein said upper support guide comprises a plurality of arms.

5. The device according to claim 4, wherein each arm of said plurality of arms extends transversely to the plane of said concave circular disc.

6. The device according to claim 4, wherein said upper support guide comprises an upper forceps connection opposite said plurality of arms and configured to receive the forceps.

7. A device for resurfacing a patella, the device comprising: a bearing framework defining a cutting slot; a lower support guide comprising first and second ends, said second end comprising a concave circular disc configured to support the patella, said first end comprises a lower forceps connection configured to receive a forceps; and an upper support guide extending parallel to a plane of said concave circular disc and configured to support the patella; said upper support guide being an integral monolithic unit with said bearing framework; said lower support guide comprising a straight medial portion between said first and second ends and being canted with respect to the plane of said concave circular disc; said upper support guide comprising a plurality of arms extending transversely to the plane of said concave circular disc; said bearing framework comprising a curved arm extending transversely to said plurality of arms.

8. The device according to claim 7, wherein said upper support guide has a plurality of openings therein.

9. The device according to claim 7, wherein the lower support guide is configured to assume a plurality of different positions with respect to a center of a patellar articular surface of the patella.

10. The device according to claim 7, wherein said upper support guide comprises an upper forceps connection opposite said plurality of arms and configured to receive the forceps.

* * * * *